US008476486B2

(12) United States Patent
Weisker et al.

(10) Patent No.: US 8,476,486 B2
(45) Date of Patent: Jul. 2, 2013

(54) ***RAMULARIA* LEAF SPOT RESISTANT SAFFLOWER**

(75) Inventors: Arthur C. Weisker, Richmond, CA (US); Gabriel Chanda Musa, Richmond, CA (US)

(73) Assignee: California Oils Corporation, Richmond, CA (US)

( * ) Notice: Subject to any disclaimer, the term of this patent is extended or adjusted under 35 U.S.C. 154(b) by 802 days.

(21) Appl. No.: 12/511,714

(22) Filed: Jul. 29, 2009

(65) Prior Publication Data

US 2011/0030105 A1    Feb. 3, 2011

(51) Int. Cl.
*A01H 1/00*  (2006.01)
*A01H 5/00*  (2006.01)
*A01H 5/10*  (2006.01)

(52) U.S. Cl.
USPC .......................... 800/260; 800/295; 800/298

(58) Field of Classification Search
None
See application file for complete search history.

(56) References Cited

U.S. PATENT DOCUMENTS 5,436,386 A   7/1995   Weisker
5,912,416 A   6/1999   Weisker

FOREIGN PATENT DOCUMENTS

EP   0648409   7/2005

OTHER PUBLICATIONS

Holdeman et al., "Diseases of Safflower, a plant disease detection aid," George E. Altstatt, Chief, Plant Pathologists in the Bureau's plant disease detection Program. Department of Agriculture. USDA circular release in 1964.
Bergman et al, "Control of *Alternaria* (*Alternaria carthami* Choud) of Safflower (*Carthamus tinctorius* L.) in the United States Northern Great Plains Region," VIth International Safflower Conference, Istanbul Jun. 6-10, 2005.
Heaton et al., "Inheritance of male Sterility in Safflower," rop Science, vol. 22, pp. 520-522 (1982).
Heller et al., "Promoting the conservation and use of underutilized and neglected crops. 7. Safflower. *Carthamus tinctorius* L.," International Plant Genetic Resources Institute (1996).
Hostert et al., "Disease Notes. First Report of *Ramularia carthami*, Causal Agent of *Ramularia* Leaf Spot of Safflower, in California," from Plant Disease, vol. 90, pp. 1260 (Sep. 2006).
Klisiewicz et al., "Common Names of Plant Diseases. Diseases of Safflower," Mar. 1993.
Klisiewicz et al., "Effect of Flooding and temperature on Incidence and severity of Safflower Seedling Rust and Viability of *Puccinia carthami* Teliospores," Disease Control and Pest Management, Phytopathology vol. 67, pp. 788-790 (1976).

*Primary Examiner* — Medina A Ibrahim
(74) *Attorney, Agent, or Firm* — Wilmer Cutler Pickering Hale and Dorr LLP

(57) ABSTRACT

The invention is directed to varieties of safflower plants and seeds that are resistant to fungal disease, such as those fungi that cause foliage diseases in *Carthamus tinctorus* l.

6 Claims, 1 Drawing Sheet

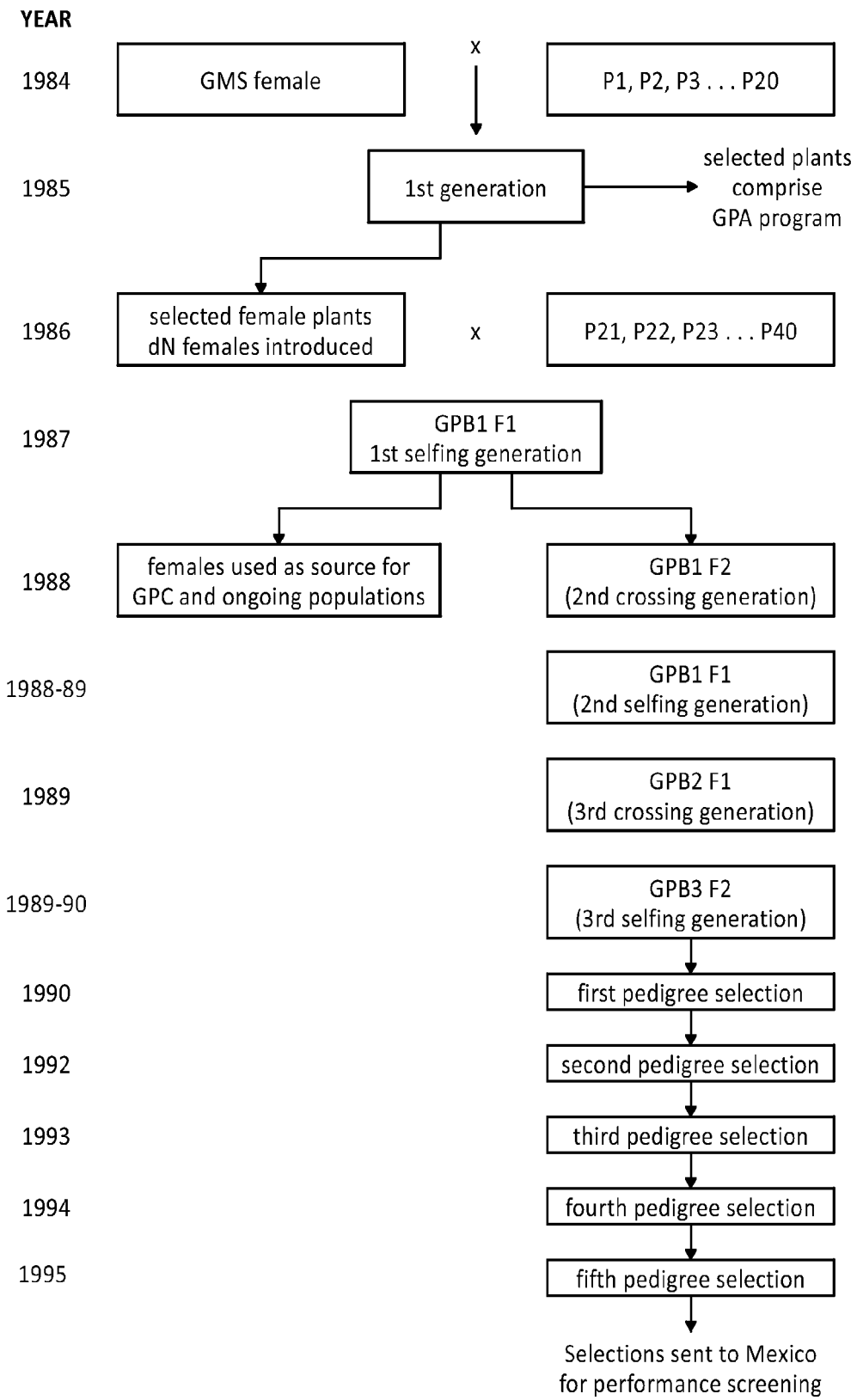

RAMULARIA LEAF SPOT RESISTANT SAFFLOWER

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is in the field of agronomy, specifically safflower breeding. The invention is directed to varieties of safflower plants and seeds that are resistant to fungus-induced foliage disease and to bacterium-induced foliage disease.

BACKGROUND OF THE INVENTION

Safflower (*Carthamus tinctorius* 1.) is a member of the compositae family. The safflower plant is a thistle-like annual with many branches, each branch having a flowerhead of bright yellow, orange or red flowers. Safflower was first cultivated in the Near East thousands of years ago. Traditionally, safflower was grown for its flowers, for use in dyes and in flavoring foods. More recently, safflower is grown for its seeds, as a source of edible oils and for use as birdseed.

Safflower was introduced to agriculture in the United States in the 1930s. With the introduction of varieties with improved oil content in the 1950s safflower found a niche in the agricultural system. Safflower is primarily grown in the United States in the Central Valley of California and in the Northern Plains States. Commercial plantings for oil are principally in the United States and Mexico, with smaller plantings in many countries whose acreage varies widely in different years. Safflower oil is a neutral tasting, colorless oil which makes it useful in blending into food products. In addition, safflower oil is very high in monounsaturated fatty acids and low in saturated fatty acids, making it a superior oil for its nutritional benefits.

BRIEF DESCRIPTION OF THE FIGURES

FIG. 1 is a flow diagram depicting various crosses carried out in order to establish the GPB proprietary population.

SUMMARY OF THE INVENTION

Through an intensive breeding program, a genetic resistance to fungus-induced foliage disease was identified in safflower. This resistance results in the resistant safflower plants staying healthy in the presence of disease pressure.

In particular, the genetic resistance of safflower of this invention is resistant to fungus-induced foliage disease caused by *Ramularia* or *Alternaria*. In another embodiment, the safflower plants of the invention are resistant to bacterium-induced foliage disease, such as foliage disease caused by the bacterium is *Pseudomonas syringae*.

The invention further relates to safflower seeds from the genetic resistant safflower plants and to all generations of succeeding progeny (plants and seeds) produced by crossing a genetic resistant safflower plant of the invention with another safflower plant.

In one aspect, the invention provides for a seed of safflower variety S-334 having ATCC Accession No. PTA-10161. In another aspect, the invention provides for a seed of safflower variety S-336 having ATCC Accession No. PTA-10162. In a further aspect, the invention provides for a seed of safflower variety S-736 having ATCC Accession No. PTA-10163. In yet another aspect, the invention provides for a seed of safflower variety S-746 having ATCC Accession No. PTA-10164. In one embodiment, a safflower plant can be grown from a seed of safflower variety S-334, S-336, S-736, or S-746. In another embodiment, a safflower seed is obtained from the plant grown from the seed of safflower variety S-334, S-336, S-736, or S-746.

In one aspect, the invention provides for a safflower plant having all of the morphological and physiological characteristics of a safflower plant derived from seed designated ATCC Accession No. PTA-10161, ATCC Accession No. PTA-10162, ATCC Accession No. PTA-10163, or ATCC Accession No. PTA-10164. In one embodiment, a safflower seed is obtained from the safflower plant having all of the morphological and physiological characteristics of a safflower plant derived from seed designated ATCC Accession No. PTA-10161, ATCC Accession No. PTA-10162, ATCC Accession No. PTA-10163, or ATCC Accession No. PTA-10164.

In one aspect, the invention provides for a safflower seed derived from a safflower line selected for resistance to a fungal-induced disease, having ATCC Accession No. PTA-10161, ATCC Accession No. PTA-10162, ATCC Accession No. PTA-10163, or ATCC Accession No. PTA-10164. In one embodiment, the disease is caused by a fungus that is caused by *Ramularia* or *Alternaria*. In another embodiment, the disease comprises *Alternaria* leaf spot, *Botrytis* head rot, *Cercospora* leaf spot, Charcoal rot, Damping-off, *Pythium* root rot, Powdery mildew, *Ramularia* leaf spot, *Rhizoctonia* blight, and stem canker or a combination of the diseases described herein. In a further embodiment, a safflower plant has all of the morphological and physiological characteristics of a safflower plant derived from the seed that is derived from a safflower line selected for resistance to a fungal-induced disease, having ATCC Accession No. PTA-10161, ATCC Accession No. PTA-10162, ATCC Accession No. PTA-10163, or ATCC Accession No. PTA-10164.

In one aspect, the invention provides for a safflower seed derived from a safflower line selected for resistance to a bacterium-induced foliage disease, having ATCC Accession No. PTA-10161, ATCC Accession No. PTA-10162, ATCC Accession No. PTA-10163, or ATCC Accession No. PTA-10164. In one embodiment, the bacterium is *Pseudomonas syringae*. In another embodiment, a safflower plant has all of the morphological and physiological characteristics of a safflower plant derived from the seed that is derived from a safflower line selected for resistance to a bacterium-induced foliage disease, having ATCC Accession No. PTA-10161, ATCC Accession No. PTA-10162, ATCC Accession No. PTA-10163, or ATCC Accession No. PTA-10164.

DETAILED DESCRIPTION OF THE INVENTION

Safflower and Foliar Diseases

Safflower grows best in areas that have well drained, deep soils with high water holding ability and in areas that are free of high atmospheric humidity for most of the growing season. These conditions need to be met largely due to the susceptibility of safflower to numerous fungal diseases, particularly diseases brought on by wet growing conditions, especially foliage diseases. Klisiewicz (1993) lists 15 fungal diseases that infect safflower. Thirteen of these diseases are water or humidity related and 10 of them attack the foliage. A USDA circular released in 1964 (Alstatt, 1964) names 23 fungal diseases worldwide. Of these fungal diseases, 17 were water or humidity related, 15 attacked the above ground foliage, and 11 are identified as leaf spot diseases: *Cercospora* leaf spot, *Ramularia* leaf spot, *Septoria* leaf spot, *Asochyta* leaf spot, *Macrosporium* leaf spot, *Stemphylium* leaf spot, *Cercosporella* leaf spot, *Cercosporina* leaf spot, *Ovularia* leaf spot, *Phyllosticta* leaf spot, and *Alternaria* leaf spot.

The best studied fungal leaf spot disease in safflower is *Alternaria carthami*. Bergman and Jacobsen (2005) list studies that have identified *Alternaria* infection in USA, Australia, Canada, India, and Mexico, with reports of infection in 13 other countries. Most other fungal diseases have received far fewer citations in literature. Due to the predominance of *Alternaria* references, combined with the general similarity of fungal leaf spot diseases, it may be the case that most observed fungal attacks that have leaf spot as a symptom that have not been definitively studied by a plant pathologist have been considered to be caused by *Alternaria*. This may lead to an underreporting of disease by other fungal organisms.

Most of the safflower production in Mexico has been in the state of Tamaulipas, with the safflower grown largely for local use and limited oil export. In the early 1990's an aggressive safflower program was begun in the Mexican state of Sonora for commercial and export use. This program included both linoleic and oleic varieties of safflower though the focus shifted primarily to oleic types by the late 1990s.

In 2000, the safflower crop was attacked by a fungal disease that caused widespread damage to the crop across all of Mexico. Studies by pathologists at CIANO, the Mexican government research organization, identified the causal organism as *Ramularia carthami*, a fungal leaf disease. The *Ramularia* leaf spot (RLS) disease was identified by leaf spots that are round and regular, a clear chestnut brown; white florescence on the lower surface of the spot becoming white due to growth of the fungus; spots may coalesce making irregular blotches. The RLS infection Mexico experienced in 2000 returned in 2001 and has been common most years since then. Studies between the government and private companies identified a number of chemical fungicides that can control the spread of RLS. Although effective, these treatments are costly, requiring as many as five treatments in a year with heavy disease presence. Prior to the Mexican RLS outbreak, RLS was rarely reported in the published literature, with infections located in France, India, Israel, Pakistan and the former Soviet Union noted (Alstatt, 1964).

Since the identification of RLS in Mexico, the disease has been identified on a number of occasions elsewhere in the Western Hemisphere. In California in 2005, RLS infection heavily damaged two fields in Northern California after a number of successive rainfalls combined with frequent early season irrigation (Hostert, 2005). RLS has also been identified in Argentina, particularly in one field located in a river basin in a year that had a number of late season rains, and in two locations in the state of Washington that had been sprinkler irrigated.

The reasons for the recent sightings of RLS are not clear. Perhaps a new, more virulent strain of *Ramularia carthami* is spreading throughout the Western Hemisphere, or the disease may have been present, but misidentified. Leaf spot diseases look superficially similar on the safflower leaf and identification can be difficult without training or a report from a pathologist. Once the disease is in advanced stage identification is more difficult since brown, dead leaves and plants are all that can be seen. The primary symptomatic differences between *Alternaria* and *Ramularia* are that *Alternaria* spots have a shotgun pattern with different colors to the leaf as the disease progresses while *Ramularia* spots are uniformly brown and the underside of the leaf has a white appearance due to the presence of fungal bodies on the underside of the leaf. The differences are apparent with training and experience but are otherwise difficult to distinguish to a casual observer.

Genetic Resistant Safflower to Fungus-Induced Foliage Disease

A wide screening of safflower germplasm was made once the identification of RLS was determined in order to find resistant sources to the disease. Nothing was found among the collection of elite germplasm from many university or commercial companies that carried significant resistance to the disease. There is no known resistance to RLS in any commercial safflower, except for the present invention. The present invention is a genetic resistance of safflower to fungus-induced foliage disease, including RLS. This genetic resistance results in the resistant safflower plants staying healthy and showing neither extreme foliar damage, reduced seed production, and other characteristics of fungal damage.

The genetic resistance of safflower of this invention is resistant to fungus-induced foliage disease caused by *Ramularia* or *Alternaria*. Non-limiting examples of safflower diseases caused by fungi include *Alternaria* leaf spot, *Botrytis* head rot, *Cercospora* leaf spot, Charcoal rot, Damping-off, *Pythium* root rot, Powdery mildew, *Ramularia* leaf spot, *Rhizoctonia* blight, and stem canker.

In another embodiment, the safflower plants of the invention are resistant to bacterium-induced foliage disease, such as foliage disease caused by the bacterium is *Pseudomonas syringae*.

Breeding for Safflower Germplasm Expansion

Safflower as an oilseed crop is relatively new. The first releases in the United States with increased oil content were developed in the late 1940s and early 1950s. Subsequent breeding has focused mainly on these lines. The result is that by the mid 1980's, the germplasm base for commercial safflower lines was quite narrow. In an attempt to broaden the germplasm base, a long term program of germplasm enhancement was begun in 1985. The method chosen was to randomly intercross selected germplasm selections from the world collection maintained by the USDA in Pullman, Wash. with select elite breeding lines.

The safflower plant is predominantly self pollinated. With self pollination, the pollen from the anthers is transferred to the stigma of the same flower, or to a flower on the same plant. To produce a hybrid from true breeding inbred male and female parents of self pollinating plants by making directed crosses requires that the female be sterile either by genetic, cytoplasmic, or mechanical sterility or by making hand emasculated crosses be genetic male sterile (GMS).

Crosses were made using GMS lines developed from the release by Heaton and Knowles (1982) or on sterile dwarf plants (Weisker, 1989; see also U.S. Pat. No. 5,436,386). As detailed in U.S. Pat. No. 5,436,386, FIG. 1 crosses were made onto sterile plants in generation 1. Generation 2 consisted of self pollinating plants from generation 1. This completed cycle one of the program. This process was repeated for two more cycles. At the end of this process, 6 generations in total, individual selections were made. These selections as a whole were given the name GPA.

Development of GPB Proprietary Population

A second population of safflower lines was begun by crossing additional germplasm selections and selected elite lines onto the first segregating population from the GPA crosses. The crossing/selfing cycle was then repeated as before with the GPA breedings. After another three cycles selections were made and these selections comprised GPB.

The breeding process continued with the GPB line using the pedigree selection method. Each year promising lines were selected in the program. Selection criteria were generally for high oil content, fatty acid composition, resistance to disease, particularly fusarium wilt, and any unique plant characteristics that may be useful in a breeding program.

The safflower plants in the GPB line had high genetic variability. This high genetic variability resulted in a much slower movement toward more uniform lines than in emasculated crosses. As a result, lines in the F5 cross were often only beginning to approach uniformity.

Developing Disease Resistant Safflower Germplasm

Developing the GBP population was the first step in exploiting expanded germplasm into superior varieties. Subsequent steps required identification of superior types in real growing situations and the ability to use this superior germplasm to make crosses that prove heritability of this germplasm into new varieties using cross pollination and selection.

Development of GPB4

In 1995 a number of safflower GPB lines were sent to Mexico to be screened in a new breeding program being established there. Superior looking lines were selected in Mexico; the best of these lines were replanted in the USA, then returned to Mexico in order to shorten the time to reach uniformity. One line in particular, GPB4-1-1-1-1-1 looked promising in Mexico due to its potential resistance to two foliar diseases, rust and *Alternaria*. Rust has been a common occurrence in Mexico while *Alternaria* was intermittent and less severe. This cycle was repeated two times. By 2000 the pedigree for the line was denoted as follows: GPB4-1-1-1-1-1-3m-4-1m-4-1m. The subscript "m" denotes a generation grown in Mexico. The above selection will be referred to as GPB4 in the following discussion.

RLS Resistance Screening

The year 2000 was the first year in which RLS infection struck in Mexico. In the breeding nursery, selections from GPB4 were among the very few safflower plants that showed resistance to RLS. In 2001, GPB4, particularly the above-described selection, was again resistant to severe RLS infestation (Table 1).

TABLE 1

Selections from GPB4 showing RLS resistance.

| Year | Source | GPB4 | Bacum |
|---|---|---|---|
| 1999-2000 | Nursery | | 7 |
| 200-2001 | Nursery | 1 | 7 |
| 2001-2002 | Nursery | 1 | 5 |
| 2002-2003 | Nursery | 1 | 5 |
| 2003-2004 | Nursery | 1 | 5 |
| 2004-2005 | Nursery | 1 | 5 |
| 2005-2006 | Nursery | 1 | 3 |

Disease reaction is rated on the following scale as shown in Table 2.

TABLE 2

Determination of Disease Reaction Score

| Scale | % Infection | Characteristic |
|---|---|---|
| 1 | 0-25% INFECTION | RESISTANT |
| 3 | 26-45% INFECTION | MODERATELY RESISTANT |
| 5 | 46-65% INFECTION | MODERATELY SUSCEPTIBLE |
| 7 | 66-85% INFECTION | SUSCEPTIBLE |
| 9 | 86-100% INFECTION | HIGHLY SUSCEPTIBLE |

Disease reaction score (% infection = damaged foliage with *Ramularia* leaf spot symptoms In 2001, the GPB4 selection was crossed onto advanced lines to determine if resistance was heritable and to create disease resistant lines with superior potential as commercial varieties. As seen in the following examples, resistance to RLS can be found in selections from the original GPB4 selection and from directed crosses of GPB4 onto varieties or experimental lines of safflower.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

The following examples are provided to further illustrate the present invention and are not intended to limit the invention beyond the limitations set forth in the appended claims.

EXAMPLE 1

Development of Safflower Variety S-746

The pedigree of S-746 is as follows: GPB4-1-1-1-1-1-3m-4-1m-4-1m-1-5-1m-1m-0m-2m-1m-0m During the selection period beginning in the 2000-2001 growing season eleven different selections that derived directly from the original GPB4 germplasm were tested. Many selections were placed into yield testing as well as nursery and disease screening. One selection in particular maintained very low levels of RLS and performed at a high level. Table 3 shows the RLS reading for S-746 compared to check lines S-719 and Bacum. S-746 has an average rating of 1.1 in 21 readings. S-719 and Bacum have readings of 4.1 and 5.7 respectively.

TABLE 3

*Ramularia* Leaf Spot (RLS) Rating, S-746
vs. S-746 and Bacum; 2005-2007

| YEAR | TRIAL | # REPS | S-746 | S-719 | Bacum |
|---|---|---|---|---|---|
| 2007 | nursery | 1 | 1 | 1 | 7 |
| 2007 | yield trial | 3 | 1 | 3 | 5 |
| 2007 | yield trial | 3 | 1 | 5 | 8.3 |
| 2007 | yield trial | 3 | 1 | 4.3 | 9 |
| 2007 | strip trial | 1 | 1 | 5 | 7 |
| 2007 | strip trial | 1 | 1 | 3 | |
| 2007 | summary | 12 | 1 | 3.6 | 7.3 |
| 2006 | nursery | 1 | 1 | 3 | 3 |
| 2006 | nursery | 1 | 1 | 3 | 3 |
| 2006 | yield trial | 3 | 1 | 9 | 7.7 |
| 2006 | yield trial | 3 | 2.3 | 4.3 | 2.3 |
| 2006 | summary | 8 | 1.3 | 4.8 | 4.0 |
| 2005 | nursery | 1 | 1 | 5 | 5 |
| 2005-07 | summary | 21 | 1.1 | 4.1 | 5.7 |

EXAMPLE 2

Development of Safflower Variety S-334

The pedigree of S-334 is as follows: (GPB4 X Bacum)-3m-1m-4Bk

In the 2000-2001 growing season in Mexico GPB4 was crossed onto Bacum. Bacum is a safflower variety that is a release of the Mexican government and was the predominant commercial safflower variety grown at that time. Bacum is a linoleic type safflower with a solid hull that is early maturing; it has relatively short stature and has a wide branching type. GPB4 at that time still segregated for fatty acid profile; it was much taller, later in maturity, and had a more acute branching pattern. The F1 and F2 generations were grown in 2002 and 2003. In 2004, the F3 selection of this cross had very low levels of RLS. In 2005, the F4 selection again had low levels of infection and was also entered into yield trials. Disease response to this selection, now named S-334, was compared to commercial oleic varieties S-518 and S-344. Table 4 shows the results of disease rating from 2005 through 2007. 2005 and 2007 were noteworthy for severe disease incidence in the Mexico. Combining three years data S-334 had a cumulative disease rating of 1.1 while susceptible commercial varieties averaged ratings of 6.4 for S-518 and 5.5 for S-344. During the test period superior selections of S-334 were grown in California for purification and increase. The line was increased in 2007 and 2008 for initial sales in Mexico for the 2009-2010 growing season.

TABLE 4

*Ramularia Leaf* Spot (RLS) Rating, S-334 vs. S-518 and S-344; 2005-2007

| YEAR | TRIAL | # REPS | S-334 | S-518 | S-344 |
|---|---|---|---|---|---|
| 2007 | Nursery | 1 | 1 | 7 | 7 |
| 2007 | Nursery | 1 | 1 | 9 | 7 |
| 2007 | Yield Trial | 3 | 1 | 7.7 | 7.7 |
| 2007 | Yield Trial | 3 | 1 | 7.7 | 5 |
| 2007 | Yield Trial | 3 | 1 | 7.7 | 7.7 |
| 2007 | Yield Trial | 3 | 1 | 8.3 | 7.7 |
| 2007 | Strip Trial | 1 | 1 | 9 | |
| 2007 | Strip Trial | 1 | 1 | 3 | |
| 2007 | Strip Trial | 1 | 1 | 7 | |
| 2007 | Average | 17 reps | 1 | 7.4 | 7.0 |
| 2006 | Nursery | 1 | 1 | 3 | 3 |
| 2006 | Nursery | 1 | 1 | 3 | 3 |
| 2006 | Yield Trial | 3 | 2.3 | 6.3 | 5 |
| 2006 | Strip Trial | 1 | 1 | 5 | 5 |
| 2006 | Strip Trial | 1 | 1 | 7 | 7 |
| 2006 | Average | 7 reps | 1.3 | 4.9 | 4.6 |
| 2005 | Yield Trial | 3 | 1 | 7 | 5 |
| 2005-2007 | average rating | 25 reps | 1.1 | 6.4 | 5.5 |

EXAMPLE 3

Development of Variety S-336

The pedigree of S-336 is as follows: (GPB4 X Bacum)-2m-5m-0m-4m-1-1

S-336 is derived from the same cross as S-334. In the F2 generation grown in 2002-2003 selection number 2 had superior resistance to RLS. Selections were made in the 2004 and 2005 nurseries to further identify selections with superior RLS resistance. Yield testing was begun in the 2004-2005 growing season. Superior selections were sent to California in 2005 for purification. Table 5 shows the disease reaction for S-336 in 2005-2007. Over the three year period 17 separate disease reading were taken. S-336 had an average disease rating of 1.0 while commercial lines S-518 and S-344 had ratings of 7.4 and 6.4 respectively.

TABLE 5

*Ramularia* Leaf Spot (RLS) Rating, S-336 vs. S-518 and S-344; 2005-2007

| YEAR | TRIAL | # REPS | S-336 | S-518 | S-344 |
|---|---|---|---|---|---|
| 2007 | Nursery | 1 | 1 | 7 | 7 |
| 2007 | Nursery | 1 | 1 | 9 | 7 |
| 2007 | Yield Trial | 3 | 1 | 7.7 | 7.7 |
| 2007 | Yield Trial | 3 | 1 | 7.7 | 5 |
| 2007 | Yield Trial | 3 | 1 | 7.7 | 7.7 |
| 2007 | Yield Trial | 3 | 1 | 8.3 | 7.7 |
| 2007 | Strip Trial | 1 | 1 | 9 | |
| 2006 | Nursery | 1 | 1 | 3 | 3 |
| 2005 | Nursery | 1 | 1 | | |
| 2005-07 | average | 17 | 1 | 7.4 | 6.4 |

EXAMPLE 4

Development of Variety S-736

The pedigree of S-736 is as follows: (GPB4 X S-719)-6m-3m-3m-0m-1-1

In the 2000-2001 growing season a selection of GPB4 was crossed onto experimental line 9055, later renamed as variety S-719. S-719, released in 2003 is a variety that was developed in the USA, but performed well Mexico. The line was in advanced testing in 2000 and showed many preferred characteristics for commercial use in Mexico. S-719 is a linoleic variety with higher oil content than Bacum and striped seed; it is relatively early maturing, of average height, and has a wide branching pattern.

The F1-F5 generations were grown during the 2002-2005 growing seasons. During this time selections were made for RLS resistance. Yield tests were conducted in 2006 and 2007 to determine overall adaptability of the line including yield and oil content as well as general phenotypic adaptability and superior RLS resistance. Table 6 shows the results of RLS disease screening from 2005-2007. S-736 had a disease rating of 1.1 while commercial S-719 and Bacum had ratings of 4.3 and 6.0, respectively. A total of 20 individual ratings were taken. F5 seed was introduced in California and grown for two years to purify the seed source and prepare for final varietal increase.

TABLE 6

*Ramularia* Leaf Spot (RLS) Rating, S-736 vs. S-719 and Bacum; 2005-2007

| YEAR | TRIAL | # REPS | S-736 | S-719 | Bacum |
|---|---|---|---|---|---|
| 2007 | nursery | 1 | 1 | 1 | 7 |
| 2007 | yield trial | 3 | 1 | 3 | 5 |
| 2007 | yield trial | 3 | 1 | 5 | 8.3 |
| 2007 | yield trial | 3 | 1 | 4.3 | 9 |
| 2007 | strip trial | 1 | 1 | 5 | 7 |
| 2007 | strip trial | 1 | 1 | 3 | |
| 2007 | summary | 12 | 1 | 3.6 | 7.3 |
| 2006 | nursery | 1 | 1 | 3 | 3 |
| 2006 | yield trial | 3 | 1 | 9 | 7.7 |
| 2006 | yield trial | 3 | 2.3 | 4.3 | 2.3 |
| 2006 | summary | 7 | 1.4 | 5.4 | 4.3 |
| 2005 | nursery | 1 | 1 | 5 | 5 |
| 2005-07 | summary | 20 | 1.1 | 4.3 | 6.0 |

Although the foregoing invention has been described in some detail by way of illustration and example for purposes of clarity and understanding, it will be obvious that certain changes and modifications may be practiced within the scope of the invention, as limited only by the scope of the appended claims.

DEPOSIT INFORMATION

A deposit of the safflower variety S-334 seed designated PTA-10161, disclosed above and recited in the appended claims, has been made with the American Type Culture Collection (ATCC), 10801 University Boulevard, Manassas, Va. 20110. The date of deposit was Jun. 30, 2009. The deposit of 2,500 seeds were taken from the same deposit maintained by the inventor since prior to the filing date of this application. All restrictions upon the deposit have been removed, and the deposit is intended to meet all of the requirements of 37 C.F.R. §1.801-1.809. The ATCC accession number is PTA-10161. The deposit will be maintained in the depository for a period of 30 years, or 5 years after the last request, or for the effective life of the patent, whichever is longer, and will be replaced as necessary during that period.

A deposit of the safflower variety S-336 seed designated PTA-10162, disclosed above and recited in the appended claims, has been made with the American Type Culture Collection (ATCC), 10801 University Boulevard, Manassas, Va. 20110. The date of deposit was Jun. 30, 2009. The deposit of 2,500 seeds were taken from the same deposit maintained by the inventor since prior to the filing date of this application. All restrictions upon the deposit have been removed, and the deposit is intended to meet all of the requirements of 37 C.F.R. §1.801-1.809. The ATCC accession number is PTA-10162. The deposit will be maintained in the depository for a period of 30 years, or 5 years after the last request, or for the effective life of the patent, whichever is longer, and will be replaced as necessary during that period.

A deposit of the safflower variety S-736 seed designated PTA-10163, disclosed above and recited in the appended claims, has been made with the American Type Culture Collection (ATCC), 10801 University Boulevard, Manassas, Va. 20110. The date of deposit was Jun. 30, 2009. The deposit of 2,500 seeds were taken from the same deposit maintained by the inventor since prior to the filing date of this application. All restrictions upon the deposit have been removed, and the deposit is intended to meet all of the requirements of 37 C.F.R. §1.801-1.809. The ATCC accession number is PTA-10163. The deposit will be maintained in the depository for a period of 30 years, or 5 years after the last request, or for the effective life of the patent, whichever is longer, and will be replaced as necessary during that period.

A deposit of the safflower variety S-746 seed designated PTA-10164, disclosed above and recited in the appended claims, has been made with the American Type Culture Collection (ATCC), 10801 University Boulevard, Manassas, Va. 20110. The date of deposit was Jun. 30, 2009. The deposit of 2,500 seeds were taken from the same deposit maintained by the inventor since prior to the filing date of this application. All restrictions upon the deposit have been removed, and the deposit is intended to meet all of the requirements of 37 C.F.R. §1.801-1.809. The ATCC accession number is PTA-10164. The deposit will be maintained in the depository for a period of 30 years, or 5 years after the last request, or for the effective life of the patent, whichever is longer, and will be replaced as necessary during that period.

What is claimed is:

1. A seed of safflower variety S-334 having ATCC Accession No. PTA-10161.

2. A seed of safflower variety S-336 having ATCC Accession No. PTA-10162.

3. A seed of safflower variety S-736 having ATCC Accession No. PTA-10163.

4. A seed of safflower variety S-746 having ATCC Accession No. PTA-10164.

5. A safflower plant grown from a seed of claim 1, claim 2, claim 3, or claim 4.

6. A safflower seed obtained from the plant of claim 5.

* * * * *